United States Patent
Kruper, Jr. et al.

(10) Patent No.: US 9,018,408 B2
(45) Date of Patent: Apr. 28, 2015

(54) PROCESSES FOR PRODUCING TEREPHTHALIC ACID AND TEREPHTHALIC ESTERS

(75) Inventors: William Kruper, Jr., Sanford, MI (US); Cynthia L. Rand, Sanford, MI (US); David C. Molzahn, Midland, MI (US)

(73) Assignee: Dow Global Technologies LLC, Midland, MI (US)

( * ) Notice: Subject to any disclaimer, the term of this patent is extended or adjusted under 35 U.S.C. 154(b) by 0 days.

(21) Appl. No.: 13/977,935

(22) PCT Filed: Jan. 10, 2012

(86) PCT No.: PCT/US2012/020744
§ 371 (c)(1),
(2), (4) Date: Jul. 2, 2013

(87) PCT Pub. No.: WO2012/125218
PCT Pub. Date: Sep. 20, 2012

(65) Prior Publication Data
US 2013/0345467 A1    Dec. 26, 2013

Related U.S. Application Data

(60) Provisional application No. 61/452,271, filed on Mar. 14, 2011.

(51) Int. Cl.
| | |
|---|---|
| *C07C 67/00* | (2006.01) |
| *C07C 69/757* | (2006.01) |
| *C07C 51/377* | (2006.01) |
| *C07C 63/26* | (2006.01) |
| *C07C 67/297* | (2006.01) |
| *C07C 67/31* | (2006.01) |
| *C07C 67/327* | (2006.01) |
| *C07C 69/675* | (2006.01) |
| *C07C 69/82* | (2006.01) |
| *C07C 67/317* | (2006.01) |

(52) U.S. Cl.
CPC ............ *C07C 69/757* (2013.01); *C07C 51/377* (2013.01); *C07C 63/26* (2013.01); *C07C 67/297* (2013.01); *C07C 67/31* (2013.01); *C07C 67/327* (2013.01); *C07C 69/675* (2013.01); *C07C 69/82* (2013.01); *C07C 67/317* (2013.01)

(58) Field of Classification Search
CPC .... C07C 69/757; C07C 67/297; C07C 67/31; C07C 67/327; C07C 69/82; C07C 69/75; C07C 51/377; C07C 63/26; C07C 67/317; C07C 69/675
USPC .......................................... 560/96, 126, 127
See application file for complete search history.

(56) References Cited

U.S. PATENT DOCUMENTS

| | | | |
|---|---|---|---|
| 2,734,077 A * | 2/1956 | Smith ........................ | 562/509 |
| 2,782,224 A | 2/1957 | Smith | |
| 3,182,078 A | 5/1965 | Mathieson | |
| 5,521,075 A | 5/1996 | Guettler et al. | |
| 5,573,931 A | 11/1996 | Guettler et al. | |
| 5,659,076 A | 8/1997 | Schwarz et al. | |
| 5,770,435 A | 6/1998 | Donnelly et al. | |
| 5,869,301 A | 2/1999 | Nghiem et al. | |
| 7,531,593 B2 | 5/2009 | Sunkara et al. | |
| 2009/0246430 A1 | 10/2009 | Kriegel et al. | |

FOREIGN PATENT DOCUMENTS

| | | |
|---|---|---|
| DE | 738922 | 9/1943 |
| GB | 731053 | 6/1955 |
| GB | 744543 | 2/1956 |
| WO | 2009064575 A1 | 5/2009 |
| WO | 2010148081 A2 | 12/2010 |
| WO | 2010151346 A1 | 12/2010 |

OTHER PUBLICATIONS

Murphy (A Carboxylic analog of Glyceraldehyde Dimer, National Institute of Arthritis and Metabolic Disease, National Institute of Health, Bethesda, Maryland, pp. 267-268, 1965.*
Written Opinion "WO" PCT/US2012/020744 2009.*
Murphy, James G.; "A Carbocyclic Analog of Glyceraldehyde Dimer"; National Institute of Arthritis and Metabolic Diseases, National Institutes of Health; Mar. 1965; pp. 267-268.
Sinnreich, Joel; "23. Chemistry of Succinyl Succinic Acid Derivatives. Part IV) On the Hydrogenation of Diethyl Succinyl Succinate"; Helvetica Chimica Acta; 1979; pp. 156-157; vol. 62.
Stolle, R.; "Ueber Die Hydrirung Des Succinylobernsteinsaureesters"; Chemische Berichte; 1990; pp. 390-392; vol. 33; Cited in the International Search Report of application No. PCT/US2012/020744 filed Jan. 10, 2012.

* cited by examiner

*Primary Examiner* — Brandon Fetterolf
*Assistant Examiner* — Blaine G Doletski
(74) *Attorney, Agent, or Firm* — Christopher A. Johnson

(57) ABSTRACT

The present invention generally relates to a condensed process for producing terephthalic acid and terephthalic esters from a dialkyl cyclohexane-2,5-dione-1,4-dicarboxylate; a chemoselective process for preparing a substantially bicyclic-lactone-free dialkyl cyclohexane-2,5-diol-1,4-dicarboxylate; and compositions of matter prepared thereby.

3 Claims, 2 Drawing Sheets

PROCESSES FOR PRODUCING TEREPHTHALIC ACID AND TEREPHTHALIC ESTERS

BACKGROUND OF THE INVENTION

The present invention generally relates to processes for producing terephthalic acid and terephthalic esters.

Terephthalic acid and terephthalic esters have been prepared from, among other things, cyclohexane-2,5-diol-1,4-dicarboxylic acid or esters thereof, which in turn have been ultimately prepared from, among other things, a dialkyl succinate, all as mentioned in patent GB 731053 or U.S. Pat. No. 2,782,224. Terephthalic acid and terephthalic esters are useful in preparing polymers such as poly(ethylene terephthalate) or PET. PET has many uses such as, for example, for making synthetic fibers and food-grade containers (e.g., beverage bottles). Methods for preparing terephthalic acid and terephthalic esters from certain biomass-derived starting materials are mentioned in WO 2010/148081 and WO 2010/151346.

A problem addressed by the present invention includes providing an alternative and improved or advantaged process for producing terephthalic acid and terephthalic esters.

BRIEF SUMMARY OF THE PRESENT INVENTION

In a first embodiment the present invention provides a condensed process for preparing a dialkyl terephthalate, the condensed process comprising a one-pot portion comprising steps (a) to (c): (a) contacting a mixture comprising dialkyl cyclohexane-2,5-dione-1,4-dicarboxylate and an oxygen-containing solvent with hydrogen ($H_2$) gas and a hydrogenating effective amount of a dual-function supported metal catalyst under hydrogenating effective conditions to give a dialkyl cyclohexane-2,5-diol-1,4-dicarboxylate, wherein the dual-function supported metal catalyst comprises a metal that can independently facilitate reduction and dehydrogenation and the metal is deposited on a solid support; (b) contacting the dialkyl cyclohexane-2,5-diol-1,4-dicarboxylate with a dehydrating effective amount of a dehydration catalyst under dehydrating effective conditions to give dialkyl dihydrobenzene-1,4-dicarboxylate; and (c) contacting the dialkyl dihydrobenzene-1,4-dicarboxylate with a dehydrogenating effective amount of the dual-function supported metal catalyst under dehydrogenating effective conditions to give a dialkyl terephthalate; wherein steps (a) to (c) are performed in a same reactor and the oxygen-containing solvent of step (a) is carried through and also employed in steps (b) and (c). If desired, additional oxygen-containing solvent(s) can be added to the reactor for step (b), (c), or both.

In a second embodiment the present invention provides a chemoselective process for preparing dialkyl cyclohexane-2,5-diol-1,4-dicarboxylate that is substantially bicyclic-lactone-free (i.e., the process is for preparing a substantially bicyclic-lactone-free dialkyl cyclohexane-2,5-diol-1,4-dicarboxylate), the chemoselective process comprising contacting a mixture comprising a dialkyl cyclohexane-2,5-dione-1,4-dicarboxylate and an oxygen-containing solvent with hydrogen ($H_2$) gas and a hydrogenating effective amount of a supported metal catalyst under hydrogenating effective conditions to give a substantially bicyclic-lactone-free dialkyl cyclohexane-2,5-diol-1,4-dicarboxylate having less than 5 weight percent (wt %) of a bicyclic lactone by-product therefrom, wherein the supported metal catalyst comprises a metal than can facilitate reduction and the metal is deposited on a solid support. Preferably, the supported metal catalyst employed in the chemoselective process is the same as the dual-function supported metal catalyst employed in the condensed process, and the chemoselective process comprises step (a) of the one-pot portion of the condensed process.

In a third embodiment the present invention provides a first composition comprising the substantially bicyclic-lactone-free dialkyl cyclohexane-2,5-diol-1,4-dicarboxylate, which has less than 5 wt % of a bicyclic lactone by-product.

In a fourth embodiment the present invention provides a second composition comprising the dialkyl dihydrobenzene-1,4-dicarboxylate and a monoalkyl dihydrobenzene-1-carboxyl-4-carboxylate, wherein the second composition is produced in step (b) of the one-pot portion of the condensed process.

In a fifth embodiment the present invention provides a third composition comprising the dialkyl terephthalate and a monoalkyl ester of terephthalic acid (i.e., monoalkyl terephthalate), wherein the third composition is produced in step (c) of the one-pot portion of the condensed process.

The dialkyl terephthalate prepared by the invention process, and any monoalkyl ester monoacid analog or terephthalic acid produced thereby, are useful in preparing polymers such as poly(ethylene terephthalate) or PET. The PET has many uses such as, for example, for making synthetic fibers and food-grade containers (e.g., beverage bottles).

The invention process provides at least one of the following advantages. The invention process is adaptable to using a petroleum- or bio-sourced feedstock, or a combination thereof, to prepare a dialkyl succinate and convert it to a dialkyl cyclohexane-2,5-dione-1,4-dicarboxylate, or an enol isomer thereof. The invention also provides a process for reducing the latter material to a dialkyl cyclohexane-2,5-diol-1,4-dicarboxylate, wherein the dialkyl cyclohexane-2,5-diol-1,4-dicarboxylate advantageously has a reduced amount, or preferably none, of a bicyclic-lactone by-product that has contaminated prior art preparations of the diol from dialkyl cyclohexane-2,5-dione-1,4-dicarboxylate. In some embodiments no bicyclic-lactone by-product can be detected (e.g., by proton NMR or, more preferably by GC-MS). Another advantage is that in some embodiments the present invention provides a condensed process comprising a "one-pot" portion for converting the starting material to the terephthalic esters, wherein the one-pot portion of the condensed process comprises sequentially a hydrogenation step, dehydration step, and then a dehydrogenation step, which steps are performed in a single reactor. The condensed process advantageously reduces the number of unit operations from 3 to 1 for this 3-step conversion. Also, the condensed process preferably gives a higher overall yield of and selectivity for the terephthalic esters. Another advantage is the condensed process can successfully employ high loadings of the dialkyl cyclohexane-2,5-diol-1,4-dicarboxylate relative to solvent. Another advantage is that overall reaction time for the three steps in the condensed process is substantially reduced versus reaction time of a comparable 3-step/3-unit operation non-invention process. Another advantage is that the condensed process can easily produce purified terephthalic acid and terephthalic esters. Still another advantage is the invention processes provides several compositions of matter that are useful in the invention processes. The compositions of matter comprise additional embodiments of the present invention.

Without wishing to be bound by theory, it is believed that the (dual-function) supported metal catalyst unexpectedly inhibits formation of the undesired bicyclic lactone by-product in the chemoselective process and, preferably, step (a) of the one-pot portion of the condensed process, and leads to an increased yield of dialkyl cyclohexane-2,5-diol-1,4-dicarboxylate. Unpredictably, the yield in step (a) can be quantitative (100%) or nearly so (e.g., >95%). It is also believed that the dual-function supported metal catalyst, or more likely, the combination of the dehydration catalyst and the dual-function supported metal catalyst together in the same reactor, unexpectedly increases overall rate of the dehydration/dehydrogenation reactions, thereby in some embodiments reducing total reaction time of the dehydration and dehydrogenation reactions from about 24 hours to less than 5 hours for a given yield of dialkyl terephthalate; and beneficially increases the yield of the dialkyl dihydrobenzene-1,4-dicarboxylate in step (b) of the one-pot portion of the condensed process. These improvements are not predictable from the prior art employing only one catalyst at a time. Also, whenever both the dialkyl cyclohexane-2,5-diol-1,4-dicarboxylate starting material of step (b) and the dialkyl dihydrobenzene-1,4-dicarboxylate starting material of step (c) are present together (i.e., shortly after initiation of step (b)), steps (b) and (c) of the condensed process are believed to be conducted concomitantly rather than sequentially, which eliminates a unit operation and decreases reaction time.

Additional embodiments are described in accompanying drawing(s) and the remainder of the specification, including the claims.

BRIEF DESCRIPTION OF THE DRAWING(S)

Some embodiments of the present invention are described herein in relation to the accompanying drawing(s), which will at least assist in illustrating various features of the embodiments.

DETAILED DESCRIPTION OF THE PRESENT INVENTION

Figure 1:
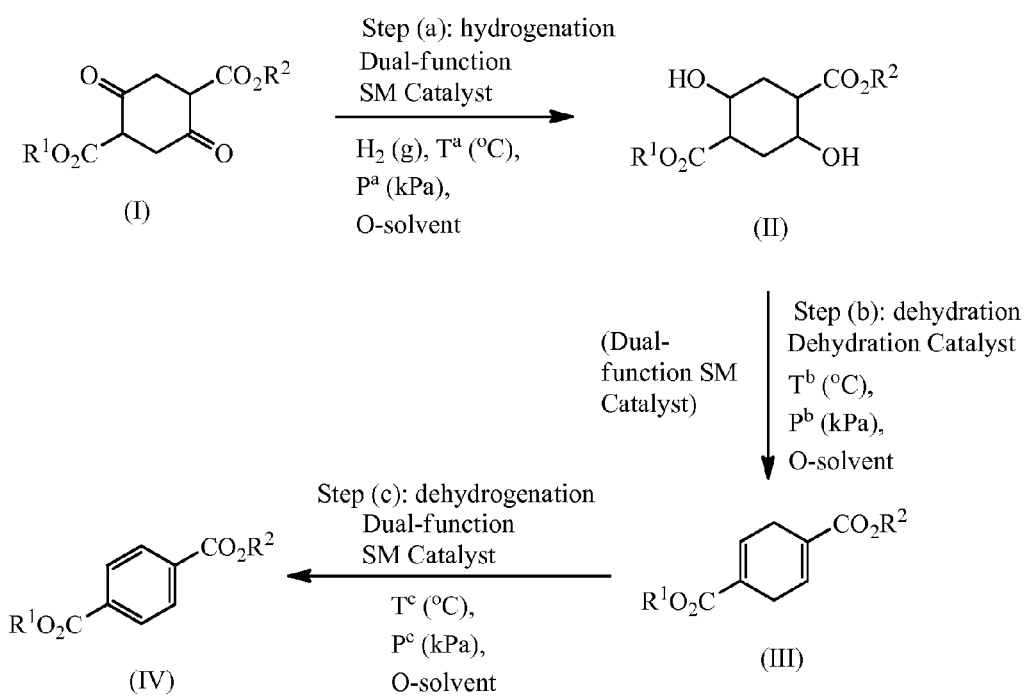
FIG. 1 illustrates steps (a) to (c) of the one-pot portion of the condensed process.

The embodiments of the present invention summarized previously and the Abstract are incorporated here by reference. As used herein, the term "alkyl" means a radical of a straight chain or branched chain, saturated hydrocarbon, preferably having from 1 to 20 carbon atoms, and more preferably at most 7 carbon atoms. Each alkyl independently is unsubstituted or substituted with a substituent that is —OH, —O-(unsubstituted alkyl), —$CO_2H$, or —$CO_2$-(unsubstituted alkyl).

The term "dialkyl cyclohexane-2,5-dione-1,4-dicarboxylate" means a compound of formula (I):

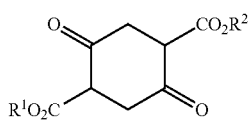

or an enol tautomer thereof, or a combination thereof.

Examples of the enol tautomer are compounds of formulas (It-1) and (It-2):

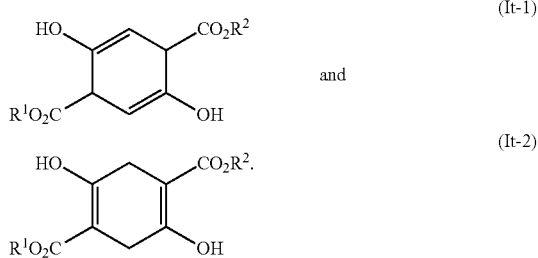

The dialkyl cyclohexane-2,5-dione-1,4-dicarboxylate can be purchased from a commercial source or readily prepared according to known methods such as the method of U.S. Pat. No. 5,783,723, e.g., Example 1.

The term "dialkyl cyclohexane-2,5-diol-1,4-dicarboxylate" means a compound of formula (II):

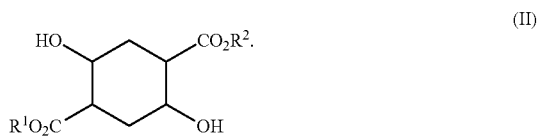

As produced in the condensed process, typically comprises a mixture of diastereomers of formula (II), wherein the major diastereomer of the mixture is characterizable by proton nuclear magnetic resonance ($^1$H-NMR) and carbon-13 nuclear magnetic resonance ($^{13}$C-NMR) as follows. $^1$H-NMR (400 MHz, CDCl$_3$): δ 4.34 (s, 1H), 3.77-3.65 (m, 3H), 3.09 (s, 1H), 2.99-2.87 (m, 1H), 2.00 (dd, J=8.1, 3.0 Hz, 2H). $^{13}$C-NMR (101 MHz, CDCl$_3$) δ 176.38, 77.29, 76.98, 76.66, 65.02, 51.88, 40.08, 28.70. As produced in the chemoselective process, or the chemoselective step (a) comprising the condensed process, the major diastereomer of formula (II) is also characterizable by x-ray crystallography as having the conformation shown below in formula (II-1):

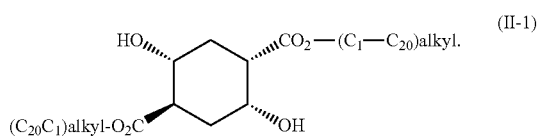

In some embodiments the chemoselective process, or the chemoselective step (a) of the condensed process produces, and the substantially bicyclic-lactone-free dialkyl cyclohexane-2,5-diol-1,4-dicarboxylate of the first composition comprises, the major diastereomer of formula (II-1).

The term "dialkyl dihydrobenzene-1,4-dicarboxylate" means a compound of formula (III):

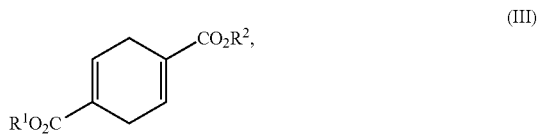

or a regioisomer thereof. In some embodiments the second composition comprises a first molar ratio of the dialkyl dihydrobenzene-1,4-dicarboxylate of formula (III) to the monoalkyl dihydrobenzene-1-carboxyl-4-carboxylate, wherein the molar ratio is derived from the first composition that comprises the major diastereomer of formula (II-1).

The term "dialkyl terephthalate" means a compound of formula (IV):

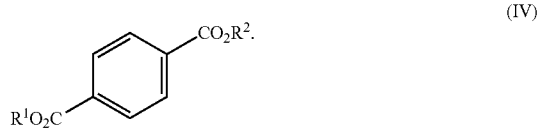

In some embodiments the third composition comprises a second molar ratio of the dialkyl terephthalate of formula (IV) to the monoalkyl ester of terephthalic acid, wherein the second molar ratio is derived from the second composition that comprises the first molar ratio of the dialkyl dihydrobenzene-1,4-dicarboxylate of formula (III) to the monoalkyl dihydrobenzene-1-carboxyl-4-carboxylate, wherein the first molar ratio is derived from the first composition that comprises the major diastereomer of formula (II-1).

In formulas (I) to (IV), each $R^1$ and $R^2$ independently is alkyl, preferably a $(C_1-C_{20})$alkyl; more preferably $(C_1-C_{10})$alkyl; still more preferably $(C_1-C_5)$alkyl; even more preferably methyl, ethyl, propyl, 1-methylethyl, or a butyl; and yet more preferably methyl. In some embodiments the alkyl is substituted with —OH (e.g., —CH$_2$CH$_2$OH). Preferably, each alkyl is —CH$_2$CH$_2$OH or methyl. In addition to employing or producing or both the compound of any one of formulas (I) to (IV), the invention processes contemplate employing, producing, or both the corresponding monoester-monoacid analog (i.e., one of $R^1$ and $R^2$ is alkyl and the other is a hydrogen atom (H)), diacid analog (i.e., both of $R^1$ and $R^2$ is H), or a combination thereof.

The term "dehydrating effective amount" means a quantity sufficient for catalyzing the conversion of the compound of formula (II) to the compound of formula (III).

The term "dehydration catalyst" means a basic substance that increases the rate of the conversion of the compound of formula (I), or an enol tautomer thereof, or a combination thereof, to the compound of formula (II), wherein the substance is not consumed in the conversion. Examples of suitable dehydration catalysts are alkali earth metal $(C_1-C_3)$ carboxylates such as sodium acetate (NaO$_2$CCH$_3$) alkali earth metal hydroxides such as sodium hydroxide (NaOH) and potassium hydroxide, and alkali earth metal alkoxides such as sodium methoxide (NaOCH$_3$), ethoxide, propoxide, or butoxide, and potassium methoxide, ethoxide, propoxide, or butoxide. Other examples of suitable dehydration catalysts include alkaline earth metal carboxylates (e.g., sodium acetate), hydroxides, and alkoxides, wherein an alkaline earth metal such as magnesium or calcium replaces two alkali earth metals in the foregoing list of alkali earth metal carboxylates, hydroxides, and alkoxides.

The term "dehydrating effective conditions" mean circumstances of the reaction comprising loss of water (—H$_2$O) from the compound of formula (II), wherein the circumstances include dehydrating temperature and dehydrating pressure. Preferably, the dehydrating temperature (sometimes represented herein as $T^b$) is from 150 degrees Celsius (° C.) to 250° C., more preferably from 170° C. to 220° C., and still more preferably from 180° C. to 210° C. (e.g., 195° C.). Preferably, the dehydrating pressure (sometimes represented herein as $P^b$) is from 14 pounds per square inch (psi; 100 kiloPascals (kPa)) to 2,000 psi (14,000 kPa) with a dehydrating pressure of up to about 1,000 psi (7,000 kPa) being preferred.

The term "dehydrogenating effective amount" means a quantity sufficient for catalyzing the conversion of the compound of formula (III) to the compound of formula (IV).

The term "dehydrogenating effective conditions" mean circumstances of the reaction comprising loss of hydrogen (—H$_2$) from the compound of formula (III), wherein the circumstances include dehydrogenating temperature and dehydrogenating pressure and egress of hydrogen gas from the container (e.g., reactor) in which the dehydrogenation is occurring. The hydrogen gas is produced as a result of the dehydrogenation, and egress thereof can be continuous or periodic. Preferably, the dehydrogenating temperature (sometimes represented herein as $T^c$) is from 150 degrees Celsius (° C.) to 250° C., more preferably from 170° C. to 220° C., and still more preferably from 180° C. to 210° C. (e.g., 195° C.). Preferably, the dehydrogenating pressure (sometimes represented herein as $P^c$) is from 300 pounds per square inch (psi; 2000 kiloPascals (kPa)) to 2,000 psi (14,000 kPa) with a dehydrating pressure of up to about 1,500 psi (10,000 kPa) being preferred. Preferably, the dehydrogenation further comprises continuous or periodic venting or purging of generated hydrogen gas (e.g., via an inert gas (e.g., nitrogen gas) stream introduced thereinto), thereby facilitating egress of the generated hydrogen gas from the reactor. In some embodiments the dehydrogenating conditions further comprise applying microwave radiation to the reactor contents, thereby increasing reaction rate thereof or yield of dialkyl terephthalate therefrom. Without being bound by theory, in some embodiments the dehydrogenation comprises a disproportionation of dialkyl dihydroterephthalate (e.g., dimethyl dihydrobenzene-1,4-dicarboxylate) to dialkyl terephthalate (e.g., dimethyl terephthalate) and dialkyl 1,4-cyclohexenedicarboxylates (e.g., dimethyl 1,4-cyclohex-1-enedicarboxylate).

The term "hydrogenating effective amount" means a quantity sufficient for catalyzing the conversion of the compound of formula (I), or the enol tautomer thereof, or the combination thereof, to the compound of formula (II).

The term "hydrogenating effective conditions" mean circumstances of the reaction comprising addition of hydrogen (+H$_2$) to the compound of formula (I), or the enol tautomer thereof, or the combination thereof, wherein the circumstances include hydrogenating temperature (sometimes represented herein as $T^a$) and hydrogenating pressure (sometimes represented herein as $P^a$). Preferably, the hydrogenating temperature is from 90 degrees Celsius (° C.) to 200° C., more preferably from 100° C. to 180° C., and still more preferably from 100° C. to 150° C. (e.g., 120° C.). Preferably, the hydrogenating pressure (total of partial pressures of hydrogen gas plus oxygen-containing solvent and any other volatile material) is from 200 pounds per square inch (psi; 2000 kiloPascals (kPa)) to 2,000 psi (14,000 kPa) with a hydrogenating pressure of up to about 1,500 psi (10,000 kPa) being preferred, and 1,200 psi being more preferred. Preferably, the hydrogenation can be performed in solution or slurry phase conditions. Typically, reaction time in the reactor for the hydrogenation step is from about 30 minutes to about 3 hours.

The phrase "metal that can facilitate reduction (hydrogenation) and dehydrogenation" means a zero valent element of any one of Groups 8, 9, or 10 of the Periodic Table of the Elements. Preferably, the Group 8 metal is ruthenium (Ru).

Preferably, the Group 9 metal is rhodium (Rh) or iridium (Ir). Preferably, the Group 10 metal is nickel (Ni) or palladium (Pd), and more preferably Pd. Preferably, the metal is the Group 8 metal, more preferably iron (Fe) or Ru, and still more preferably Ru. It is believed that the Ru is especially advantageously effective for use in the chemoselective process to minimize or, preferably, avoid production of the bicyclic lactone by-product; avoid reduction of the carboxylate moieties of the dialkyl cyclohexane-2,5-dione-1,4-dicarboxylate, or, more preferably both. In some embodiments the metal is Ir, Ni, Ru, Rh, Pd, Pt, or a combination thereof; Ir, Ru, Pt, Pd, or a combination thereof; Ru, Rh, Pd, or a combination thereof; Rh or Ru or a combination thereof; Rh or Pd or a combination thereof; Pd or Ru or a combination thereof; Ni or Ru or a combination thereof; or the metal consists essentially of Rh; or the metal consists essentially of Ru and Pd; or the metal consists essentially of Ru; or the metal consists essentially of Pd. The metal is loaded on the solid support in any effective amount, which typically is from 0.05 wt % to 20 wt %; from 0.1 wt % to 15 wt %; from 0.5 wt % to 12 wt %; from 1.0 wt % to 10 wt %; or from 1.8 wt % to 5.5 wt % (e.g., 2 wt % or 5 wt %). Ratio of weight of catalyst to weight of substrate (e.g., dialkyl cyclohexane-2,5-dione-1,4-dicarboxylate) is any effective amount, which typically is from 0.001% to 5%; from 0.002% to 3%; from 0.005% to 2%; from 0.010% to 1.7%; or from 0.10% to 1.5%.

The term "oxygen-containing solvent" means an organic liquid comprising carbon, hydrogen, and at least one oxygen atom. In some embodiments the oxygen-containing solvent further comprises a nitrogen atom. In other embodiments the oxygen-containing solvent consists of hydrogen, oxygen and carbon atoms. Preferably, the organic liquid is pH neutral and has at most 20 carbon atoms, and more preferably at most 10 carbon atoms. Examples of preferred oxygen-containing solvents are carboxamides (e.g., N,N-dimethylformamide and N,N-dimethylacetamide); alkanols (e.g., methanol and monoethylene glycol), preferably an alkanol corresponding to the alkyl(s) of $R^1$ and $R^2$); ethers, including cyclic ethers (e.g., tetrahydrofuran) and diglyme; hydroxyethers (e.g., 1-methoxy-2-propanol); and carboxylic esters (e.g., ethyl acetate and alkyl esters of lactic acid such as methyl lactate).

The term "reactor" means a vessel suitable for conducting the aforementioned reactions and can be a batch, semi-batch, plug-flow, continuous-flow, and continuous stir type of reactor. In the condensed process the reactor is compatible with each of the steps (a) to (c) thereof. Preferably, the reactor is configured in such a way so as to enable at least one, preferably at least two, and more preferably at least three of the following: measuring of temperature of the contents therein; measuring of pressure therein; introduction of ingredients separately or as a mixture; purging thereof by an inert gas (e.g., nitrogen gas) or charging with a reactant gas (e.g., hydrogen gas); when desired, egress of hydrogen gas therefrom (e.g., excess hydrogen gas from the hydrogenation step or hydrogen gas produced in the dehydrogenation step); introduction of the ingredients (e.g., dehydration catalyst) as a liquid, solid, or slurry; and, in a stirred reactor, rapid stirring of reactor contents via a stir shaft and impeller rotating at a stirring rate of at least 500 revolutions per minute (rpm).

The term "solid support" means a finely divided substance of definite shape and volume (not gaseous or liquid) suitable for hosting (functionally inert to) the metal that can facilitate reduction and dehydrogenation. Examples of suitable solid supports are finely divided carbon, silica, alumina, aluminosilicates, and zeolites. Preferably, the solid support is finely divided carbon.

The term "supported metal catalyst" means a homogeneous or a heterogeneous catalytic material containing a metal that can facilitate reduction and dehydrogenation and that can be used to increase the rate of the conversion of the compound of formula (I) to the compound of formula (II), the compound of formula (III) to the compound of formula (IV), or, when the supported metal catalyst is the dual-function supported metal catalyst, both (typically at different times). In the homogenous catalytic material the metal is coordinated by a solubilizing ligand in such a way that the homogeneous catalytic material can dissolve in the oxygen-containing solvent, especially at reaction temperature. Preferably, the supported metal catalyst is the heterogeneous catalytic material, wherein the metal is deposited on a solid support and is substantially insoluble in the oxygen-containing solvent at ambient temperature. More preferably, the supported metal catalyst is the dual-function supported metal catalyst that is the heterogeneous catalytic material. Advantageously once reaction is complete, the heterogeneous catalytic material can be removed from a reaction mixture by filtration, thereby giving a filtrate comprising product and substantially or completely lacking the heterogeneous catalytic material. Preferably, the supported metal catalyst is substantially not leachable to a reaction product or solvent.

The phrase "substantially bicyclic-lactone-free dialkyl cyclohexane-2,5-diol-1,4-dicarboxylate" means the first composition comprising the compound of formula (II) and having less than 5 mole percent or 5 weight percent of the bicyclic lactone of formula (L):

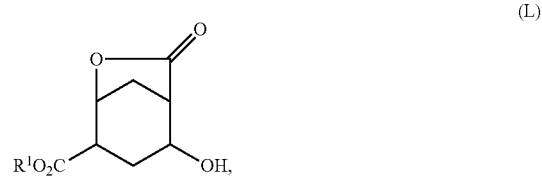

wherein $R^1$ independently is as defined for formula (I) or (II) or $R^1$ is H. Where there are two bicyclic lactones of formula (L), the total thereof is less than 5 wt % in the first composition. Preferably, the first composition has less than 2 wt %, more preferably less than 1 wt % of the bicyclic lactone of formula (L).

Any open-ended term "comprising" or "comprises" may be replaced by the respective partially closed phrase "consisting essentially of" and "consists essentially of" or the respective closed phrase "consisting of" and "consists of" to give another embodiment of the invention.

Conflict resolution: what is written in the present specification controls any conflict with what is written in a patent, patent application, or patent application publication, or a portion thereof that is incorporated by reference. The structure controls any conflict with a compound name. Any non-international system of units value controls any conflict with an International System (SI) of Units value. The drawing controls any conflict with the written description thereof.

Numerical ranges: any lower limit of a range of numbers, or any preferred lower limit of the range, may be combined with any upper limit of the range, or any preferred upper limit of the range, to define a preferred aspect or embodiment of the range. Unless otherwise indicated, each range of numbers includes all numbers, both rational and irrational numbers, subsumed in that range (e.g., "from 1 to 5" includes, for example, 1, 1.5, 2, 2.75, 3, 3.81, 4, and 5).

Unless otherwise noted, the phrase "Periodic Table of the Elements" refers to the official periodic table, version dated Jun. 22, 2007, published by the International Union of Pure and Applied Chemistry (IUPAC). Also any references to a Group or Groups shall be to the Group or Groups reflected in this Periodic Table of the Elements.

FIG. 1 shows steps (a) to (c) of the one-pot portion of the condensed process. In FIG. 1, the compound of formula (I) is hydrogenated according to step (a) of the condensed process to give the compound of formula (II), which in turn is dehydrated according to step (b) of the condensed process to give the compound of formula (III), which in turn is dehydrogenated according to step (c) of the condensed process to give the compound of formula (IV), wherein steps (a) to (c) are performed in a same reactor. Preferably, the $H_2$ gas is removed from the reactor before step (b). Preferably, steps (b) and (c) are performed under an inert gas atmosphere (e.g., a gas of nitrogen, argon, helium, or a mixture thereof). In some embodiments wherein the O-solvent (oxygen-containing solvent) of step (a) preferably has a boiling point above $T^a$ or $T^b$, whichever is lower, the $H_2$ gas in step (a) is removed from the reactor by purging the reactor with the inert gas; then the dehydration catalyst is added (e.g., via injection through a reactor port) into the reactor, wherein temperature of the reactor contents is preferably below the lower of $T^a$ or $T^b$; and then steps (b) and (c) are run. Thus, steps (b) and (c) can be run without needing to cool, and preferably without cooling, the reactor contents to ambient temperature before adding the dehydration catalyst and reheating reactor contents.

In some embodiments the high loading of the dialkyl cyclohexane-2,5-diol-1,4-dicarboxylate relative to solvent means from 20 wt % to 50 wt %, from 20 wt % to 40 wt %, from 30 wt % to 50 wt %, from 20 wt % to 30 wt %, from 30 wt % to 40 wt %, or from 40 wt % to 50 wt % of the dialkyl cyclohexane-2,5-diol-1,4-dicarboxylate relative to solvent.

In addition to dialkyl terephthalate, the invention process typically also produces monoalkyl ester of terephthalic acid and, in some embodiments, terephthalic acid. If desired the dialkyl terephthalate can be readily separated from the monoalkyl ester of terephthalic acid and terephthalic acid by crystallization of the dialkyl terephthalate from the reaction mixture, which optionally can be diluted with an alkanol to produce additional crops of crystalline dialkyl terephthalate. As used herein, the term "alkanol" means an aliphatic hydrocarbon containing at least one, and preferably at most 2, hydroxyl (—OH) groups.

In some embodiments the invention composition is as described in any one of the ad rem Examples of the present invention that are described later.

In some embodiments the dialkyl cyclohexane-2,5-dione-1,4-dicarboxylate of formula (I) (and the enol tautomer(s)) is obtained from a commercial supplier such as TCI America Inc., Portland, Oreg., USA (part of Tokyo Chemical Industry, Tokyo, Japan). In other embodiments the condensed process and chemoselective process independently further comprise preliminary steps of preparing the dialkyl cyclohexane-2,5-dione-1,4-dicarboxylate. In such embodiments the dialkyl cyclohexane-2,5-dione-1,4-dicarboxylate is preferably prepared from a succinic acid or, more preferably, a dialkyl succinate. It is not critical how the dialkyl cyclohexane-2,5-dione-1,4-dicarboxylate is prepared. For example in a condensation reaction, the dialkyl succinate can be contacted with a condensing agent such as, for example, an alkali or alkaline earth metal alkoxide, preferably wherein the alkoxide portion corresponds to the alkyl portion(s) of the dialkyl succinate (e.g., the alkali earth metal alkoxide is $NaOCH_3$ when the dialkyl succinate is dimethyl succinate) in the oxygen-containing solvent, preferably an alkanol corresponding to the alkoxide portion of the alkali or alkaline earth metal alkoxide, under condensing effective conditions (e.g., oxygen-containing solvent reflux temperature and ambient pressure under an inert atmosphere such as nitrogen gas or argon gas) so as to give a corresponding alkali or alkaline earth metal salt of the dialkyl cyclohexane-2,5-dione-1,4-dicarboxylate, which salt can then be neutralized, if desired, with 2 mole equivalents of a Brønsted acid (e.g., HCl or acetic acid) so as to give the dialkyl cyclohexane-2,5-dione-1,4-dicarboxylate. The dialkyl succinate used in the condensation reaction can be readily prepared in very high yield (typically >95% yield, and including 100% yield) from the succinic acid by heating succinic acid in a corresponding alkanol in the presence of an acid catalyst (e.g., para-toluenesulfonic acid) under dehydrating conditions and with removal of water (e.g., via a Dean-Stark trap or a solid drying agent) to give the dialkyl succinate. In much the same way, a second dialkyl succinate can be prepared from the dialkyl succinate via transesterification in a second corresponding alcohol. By "corresponding alkanol" is meant methanol for dimethyl succinate, ethanol for diethyl succinate, and the like.

It is not critical how the succinic acid or dialkyl succinate is prepared. The succinic acid and a dialkyl succinate can be obtained from the petroleum- or bio-sourced feedstock (i.e., biomass), or a combination thereof. Succinic acid and dialkyl succinate derived from the petroleum-sourced feedstock can be obtained from a commercial source such as Sigma-Aldrich Company, St. Louis, Mo., USA. Preferably, the succinic acid or a dialkyl succinate is prepared from the bio-sourced feedstock, e.g., a renewable plant material; and are respectively referred to herein as biosuccinic acid and dialkyl biosuccinate. Preparation of biosuccinic acid typically comprises fermentation of sugar or ammonium tartrate or other biological material, whereby biosuccinic acid is naturally produced as a by-product. Examples of suitable biological materials for preparing biosuccinic acid are sugars, starches, corns, cellulosics, lignocelluosics, hemicelluloses, potatoes, plant oils, polysaccharides such as pectin, chitin, levan, or pullulan, and a combination thereof. In some embodiments the biosuccinic acid is prepared according to a process of any one of U.S. Pat. No. 5,521,075; U.S. Pat. No. 5,573,931; U.S. Pat. No. 5,770,435; and U.S. Pat. No. 5,869,301. Dialkyl biosuccinate can be readily prepared from biosuccinic acid by heating biosuccinic acid in a corresponding alkanol in the presence of an acid catalyst (e.g., para-toluenesulfonic acid) and with removal of water (e.g., via a Dean-Stark trap or a solid drying agent) to give the dialkyl biosuccinate. In much the same way, a second dialkyl biosuccinate can be prepared from the dialkyl biosuccinate via transesterification in a second corresponding alcohol. By "corresponding alkanol" is meant methanol for dimethyl biosuccinate, ethanol for diethyl biosuccinate, and the like. Alternatively, biosuccinic acid and dialkyl biosuccinate can be obtained from a commercial source such as, for example, BioAmber Inc., Plymouth, Minn., USA.

The biosuccinic acid and dialkyl biosuccinate can be distinguished from succinic acid and dialkyl succinate derived from the petroleum-sourced feedstock by their higher carbon-fourteen (C-14) content. C-14, which has a half life of about 5,700 years, is found in biosuccinic acid and dialkyl biosuccinate, but C-14 is not found, or is found in trace amounts, in succinic acid and dialkyl succinate derived from the petroleum-sourced feedstock. C-14 levels of a material can be determined by measuring the material's C-14 decay process through liquid scintillation counting. The decay process of the material typically is expressed in units of disintegrations per minute per gram carbon (dpm/gC), wherein gram carbon is weight in grams of the carbon that the material contains.

The decay process for succinic acid and dialkyl succinate 100% derived from the petroleum-sourced feedstock would be <0.2 dpm/gC, and typically <0.1 dpm/gC. The decay process for 100% biosuccinic acid or 100% dialkyl biosuccinate would be expected to be >10 dpm/gC, and typically about 15 dpm/gC. The decay process for the combination of petroleum-derived succinic acid and biosuccinic acid, or the combination of petroleum-derived dialkyl succinate and dialkyl biosuccinate, would be from >0.2 dpm/gC to about 15 dpm/gC, depending upon relative proportion thereof.

In some embodiments the invention relates to intermediate compounds and products (e.g., the dialkyl terephthalate and terephthalic acid) prepared by the steps of the processes described herein. Preferably, the intermediate compound is the dialkyl cyclohexane-2,5-dione-1,4-dicarboxylate; dialkyl cyclohexane-2,5-diol-1,4-dicarboxylate; or dialkyl dihydrobenzene-1,4-dicarboxylate. In some embodiments the intermediate compound is the substantially bicyclic-lactone-free dialkyl cyclohexane-2,5-diol-1,4-dicarboxylate. In any such embodiments wherein the starting succinic acid is the biosuccinic acid prepared from biomass, the resulting intermediate compounds and products will contain a significant percentage of carbon atoms derived from biomass and a detectable trace or greater amount of carbon-14, preferably up to about 1 part per trillion. Such biosuccinic acid and resulting biomass-derived intermediate compounds are unique and distinguishable by their detectable trace or greater amount of carbon 14, as determined according to ASTM D6866-10, from corresponding compounds derived from petroleum-based sources (e.g., fossil fuel sources). The term "ASTM D6866-10" means the year 2010 method, *Standard Test Methods for Determining the Biobased Content of Solid, Liquid, and Gaseous Samples Using Radiocarbon Analysis*, that is promulgated by ASTM International, West Conshohocken, Pa., USA. Alternatively, the biosuccinic acid and resulting biomass-derived intermediate compounds and products can be distinguished from corresponding compounds derived from petroleum-based sources by method (a) or (b): (a) carbon-14 accelerator mass spectrometry (AMS) with results expressed in units of fraction of modern carbon ($f_m$), wherein $f_m$ is National Institute of Standards and Technology (NIST) Standard Reference Materials 4990B and 4990C, all as described in U.S. Pat. No. 7,531,593 B2 column 7, lines 1 to 41; (b) by carbon-13/carbon-12 ratio as described in U.S. Pat. No. 7,531,593 B2 column 7, line 42, to column 8, line 29. All of these methods of distinguishing are useful singly or in combination for, among other things, tracking these materials in commerce, monitoring competitor activities for potential infringement, and determining shelf-life and environmental impact of end products prepared therefrom (e.g., an end-product poly(ethylene terephthalate) prepared from the dialkyl terephthalate prepared from the intermediate compounds prepared from the biosuccinic acid).

In some embodiments the biomass-derived intermediate compounds named in the immediately preceding paragraph independently contain 6 or more carbons, more preferably 8 or more carbons, derived from biomass. Preferably each of the 6 carbons derived from biomass are the carbon atoms of the previously drawn 6-membered carbocyclic rings of the biomass-derived intermediate compounds. In embodiments wherein the intermediate compounds are utilized to prepare the dialkyl terephthalate that is in turn used to prepare polymers (e.g., a poly(ethylene terephthalate), the monomer units of the polymers preferably contain 6 or greater carbons, and more preferably 8 or greater carbons, derived from biomass.

When the dialkyl biosuccinate or biosuccinic acid is used to prepare the starting material, the condensed process can be said to produce dialkyl bioterephthalate or a mixture thereof with monoalkyl ester of bioterephthalic acid and, optionally, bioterephthalic acid.

The dialkyl terephthalate or a mixture thereof with monoalkyl ester of terephthalic acid and, optionally, terephthalic acid is useful for preparing a PET. The PET can be prepared by well-known means by polymerizing monomers comprising dialkyl terephthalate and monoethylene glycol. Additional monomers can be further used. Examples of the additional monomers are diethylene glycol; cyclohexanedimethanol; dialkyl isophthalate or monoalkyl ester-mono acid or isophthalic acid or combination thereof.

The PET is typically prepared sequentially employing five reactors comprising first and second esterification reactors and first, second, and third polycondensation reactors. The first and second esterification reactors and first, second and third polycondensation reactors are sequentially in operative connection to, and in at least periodic fluid communication with, each other. The PET manufacturing process uses the dialkyl terephthalate or a mixture thereof with monoalkyl ester of terephthalic acid and, optionally, terephthalic acid that is prepared by the condensed process and initially produces ethylene terephthalate oligomers, which are then polycondensed so as to produce PET. Preferably, the PET manufacturing process employs a solid state polycondensation step downstream from the polycondensation step of the third polycondensation reactor. Still more preferably, the ingredients (PET monomers and oligomers) are kept in the first and second esterification reactors and first polycondensation reactor for an average residence time and are continuously flowed through the second and third polycondensation reactors. Preferably, pressure in each of the reactors is decreased in a stepwise fashion from one reactor to the next reactor in the series, starting at a pressure from slightly greater than ambient pressure to 0.5 bar (50 kilopascals (kPa, preferably 90 kPa to 50 kPa) in the first esterification reactor and ending with approximately 1 millibar (0.1 kPa) pressure in the third polycondensation reactor. Preferably, temperature of contents in the reactors is increased in a stepwise fashion going from one reactor to the next reactor in the series, starting at a temperature of from about 255° C. to about 265° C. in the first esterification reactor (i.e., the first container) and ending with a temperature of from about 265° C. to about 285° C. in the third polycondensation reactor. The PET manufacturing process employs a suitable polycondensation catalyst in the reactors. Examples of suitable polycondensation catalysts are antimony trioxide, germanium dioxide, titanium alcoholates (e.g., titanium ($C_1$-$C_5$)alcoholates), or a combination thereof. Optionally, the PET manufacturing process can also employ at least one additive so as to produce a PET containing the at least one additive. Examples of suitable additives are a colorants, heat stabilizers, fast reheat additives, gas barrier additives, ultraviolet light blocking additives, and optical brighteners. In this way the dialkyl terephthalate or a mixture thereof with monoalkyl ester of terephthalic acid and, optionally, terephthalic acid prepared by the invention process is used to manufacture PET, which optionally contains at least one additive. Preferably, the PET is a bioPET, which means a PET that is prepared from the dialkyl bioterephthalate or a mixture thereof with monoalkyl ester of bioterephthalic acid and, optionally, bioterephthalic acid.

Once manufactured, the PET can be processed so as to produce a PET resin. The PET resin can then be molded (e.g., injection molded or stretch blow molded) so as to produce a PET container. The bioPET can be processed to produce a bioPET resin, which can be injection molded or stretch blow molded so as to produce a bioPET container.

In some embodiments the condensed process further comprises steps of manufacturing PET, preferably bioPET, processing the PET into a PET resin, preferably a bioPET resin, and molding the PET resin, preferably the bioPET resin, into a PET container, preferably a bioPET container. Preferably, the PET container is of a grade suitable for use as a food or beverage container. Gas chromatography (GC): Rtx-1701 (15 meter (m), 320 μm inner diameter (i.d.), 0.50 μm film thickness) (100° C. (0 minutes) 17° C./minute to 270° C. (5 minutes), He gas carrier, split ratio 100/1. For product of step (a) of condensed process, GC analysis conditions are: Oven profile 200° C. (6 minutes) 30° C./minute to 270° C. (3 minutes), inlet temperature 200° C., He carrier gas (5.37 psig, 1.6 mL/minute), split ratio 50/1, detector temperature 300° C. Using this method the four dimethyl 2,5-dihydroxycyclohexane-1,4-dicarboxylate isomers elute at 7.07 minutes, 7.35 minutes, 7.50 minutes, and 8.43 minutes. The bicyclic lactone by-product (impurity) elutes at 7.40 minutes. For product of steps (b) and (c) of condensed process, the GC analysis conditions are: Oven profile 100° C. (0 minutes) 17° C./minute to 270° C. (5 minutes), inlet temperature 200° C., He carrier gas (5.37 psig, 1.6 mL/minute), split ratio 50/1, detector temperature 300° C. Using this method dimethyl terephthalate elutes at 6.55 minutes; dimethyl cyclohexene-1,4-dicarboxylate elutes at 6.61 minutes; dimethyl cyclohexa-1,3-diene-1,4-diccarboxylate elutes at 6.76 minutes; and dimethyl cyclohexa-2,5-diene-1,4-diccarboxylate elutes at 7.10 minutes.
Gas chromatography/mass spectrometry (GC-MS, medium resolution): Inject one microliter aliquots of the sample as 10 milligrams per milliliter (mg/mL) solutions in 1:1 (N,O-bis(trimethylsilyl)trifluoroacetamide/pyridine derivatization reagent (BSTFA/pyridine, for converting hydroxyl groups to O-trimethylsilyl groups) onto an Agilent 6890N GC coupled to a Micromass GCT, SN CA095, time of flight GC/MS system in electron impact (EI) ionization and chemical ionization (CI) PCI-NH3 modes. Use the following analysis conditions: Column: 30 meters (m)×0.250 millimeters (mm) (0.25 micron (μm) film, Rxi-5SilMS; Temperatures: Column 60° C. (2 minutes) to 320° C. at 10° C./minute (hold 10 minutes); Injector is 280° C.; GC Re-entrant 280° C.; Source 180° C./120° C. (EI/CI); Flow: Flow 1.2 mL/minute (He gas), constant flow; Split 100:1; Detector: MCP 2350 volts (V), Mode is TOFMS, CENT, Resolution is 9000 (at m/z 614), Electron Energy is 70 electron volts (eV)/100 eV (EI/CI), Trap current is 150 microAmperes (μA) (EI), Emission Current is 1500 μA (CI), Scan is 35 atomic mass units (amu) to 800 amu (EI) or 60 amu to 900 amu (CI), and Rate is 0.5 second/scan; Lock Mass: 201.9609 $C_6F_5Cl$ (+); and Source Pressure: 2.5E-5 Torr ammonia.

X-ray analysis is performed as described here.

Data Collection: A single crystal of suitable dimensions is immersed in oil, PARATONE® N (Chevron Intellectual Property LLC), available from Exxon Chemicals, Inc., and mounted on a thin glass fiber. The crystal is transferred to a Bruker SMART™ Platform diffractometer equipped with a graphite monochromatic crystal, a MoKα radiation source (λ=0.71073 Å), and a CCD (charge coupled device) area detector. The crystal is bathed in a cold nitrogen stream for the duration of data collection (−100° C.).

Program SMART™ (available from Bruker AXS, Inc., Madison, Wis., USA) is used for diffractometer control, frame scans, indexing, orientation matrix calculations, least squares refinement of cell parameters, crystal faces measurements and the actual data collection. Program ASTRO™ (available from Bruker AXS, Inc., Madison, Wis., USA) is used to set up data collection strategy.

Raw data frames are read by program SAINT™ (available from Bruker AXS, Inc., Madison, Wis., USA) and integrated using 3D profiling algorithms. The resulting data are reduced to produce hid reflections and their intensities and estimated standard deviations. The data are corrected for Lorentz and polarization effects. Sufficient reflections are collected to represent a range of 1.51 to 2.16 redundancy level with an $R_{sym}$ value range of 2.5 percent, at the lowest 2θ shell of reflections, to 3.0 percent at the highest 2θ shell of reflections (55°). Crystal decay correction is applied and is less than 1 percent. The unit cell parameters are refined by least squares of the setting angles of the reflections.

Absorption corrections are applied by integration based on indexed measured faces. Data preparation is carried out using program XPREP™ (available from Bruker AXS, Inc., Madison, Wis., USA). The structure is solved by direct methods in SHELXTL5.1™ (available from Bruker AXS, Inc., Madison, Wis., USA) from which the positions of all of the non-H atoms are obtained. The structure is refined, also in SHELXTL5.1™, using full-matrix least-squares refinement. The non-H atoms are refined with anisotropic thermal parameters and all of the H atoms are calculated in idealized positions and refined riding on their parent atoms, or are obtained from a Difference Fourier map and refined without any constraints. A correction for secondary extinction is not applied. The final refinement is carried out using $F^2$ rather than F values. $R_1$ is calculated to provide a reference to the conventional R value but its function is not minimized. Additionally, $wR_2$ is the function that is minimized, and not $R_1$.

The linear absorption coefficient, atomic scattering factors and anomalous-dispersion corrections are calculated from values from the International Tables for X-ray Crystallography (1974). Vol. IV, p. 55. Birmingham: Kynoch Press (Present distributor, D. Reidel, Dordrecht).

Relevant Functions:

$R_1 = \Sigma(||F_o|-|F_c||)/\Sigma|F_o|$ $wR_2 = [\Sigma[w(F_o^2-F_c^2)^2]/\Sigma[wF_o^{2\,2}]]^{1/2}$ $R_{int.} = \Sigma|F_o^2-F_o^2(\text{mean})|^2/\Sigma[F_o^2]$ $S = [\Sigma[w(F_o^2-F_c^2)^2]/(n-p)]^{1/2}$ where n is the number of reflections and p is the total number of parameters refined $w = 1/[\sigma^2(F_o^2)+(0.0370*p)^2+0.31*p], p=[\max(F_o^2,0)+2*F_c^2]/3.$ Some embodiments of the invention are described in more detail in the following Examples.

Example 1

Condensed Process

Slurry dimethyl cyclohexane-2,5-dione-1,4-dicarboxylate (also known as disuccinate dimethyl ester; assayed by proton nuclear magnetic resonance (proton NMR, 400 MegaHertz (MHz)) as being in form of a bis-enol tautomer in $CDCl_3$) from TCI America (50.0 g, 0.219 mol) in 150 mL of methanol, and add 350 mg of Strem 5 wt % Ru on carbon (Ru/C) to a 300 mL volume stainless steel Parr reactor fitted with a stirrer, closable side-arm septum port, and needle valve. Seal the reactor, and pressurize it to 500 psig with $H_2$ gas, then vent, and repeat this sealing/pressurizing/venting 3 times to give a $H_2$ gas pressurized and sealed reactor. Heat contents of the reactor to 120° C., and pressurize the heated reactor with additional H₂ gas to 1000 psig to 1100 psig with stirring throughout at 800 revolutions per minute (rpm). Observe a pressure drop to about 800 psig, and recharge the reactor with additional H₂ gas to 1000 psig to 1100 psig, and repeat this pressure drop/recharging over a 5 hour period. Allow the reactor to run overnight at 1000 psig and 120° C. with no further H₂ gas uptake. After a total of 16 hours 120° C. and 1000 psig, vent the reactor, and reduce temperature to 25° C. by cooling the reactor. To the resulting cooled reactor contents add a solution of 1.5 g of NaOH in 30 mL of MeOH through the side-arm septum port, and purge the reactor 5 times with nitrogen gas (45 psig). Heat the reactor contents to 195° C. for 2 hours. Observe a increase in reactor pressure to 1000 psig, and maintain this pressure by cautiously venting the reactor through the needle valve. Then cool the reactor to 25° C., and vent the cooled reactor. Retrieve the contents comprising a grey-white slurry from the reactor, and wash the contents with about 400 mL of MeOH. Observe that a residual grey-white solid remains insoluble and is filtered off using a medium-porosity sintered glass fitted funnel. Total MeOH wash is about 700 mL. Remove the methanol on a rotary evaporator to yield 38 g of a crude, light yellow semi-solid material (89%); ¹H-NMR (400 MHz, CDCl₃ indicates the material consists essentially of a 1:2:1 molar ratio of dimethyl terephthalate to dimethyl dihydroterephthalate isomers to dimethyl tetrahydroterephthalate; (and <1 mol % methyl benzoate). Add 700 mL of MeOH with stirring to this material, and place the resulting solution in the freezer (–20° C.) to give 2 crops of white crystals (mp=140° C.-142° C.) of dimethyl terephthalate (total 10.0 g, 24% yield) (contains a small amount of dimethyl dihydroterephthalate by ¹H-NMR (400 MHz, CDCl₃). δ 8.09 (s, 4H), 3.94 (s, 6H); ¹³C-NMR (101 MHz, CDCl₃) δ 166.23, 133.90, 129.50, 52.36.

Chromatographic fractionation of the MeOH liquor (using methylene chloride and flash silica gel) provides, if desired, analytically pure samples of the dimethyl terephthalate; dimethyl dihydroterephthalate isomers; and dimethyl tetrahydroterephthalate. Observe that no identifiable bicyclic lactone by-product is isolated or observed by ¹H-NMR (400 MHz, CDCl₃) or by GC-MS.

Example 2

Chemoselective Process

Load dimethyl cyclohexane-2,5-dione-1,4-dicarboxylate (also referred to herein as dimethyl-2,5-dihydroxy-cyclohexa-2,5-diene dicarboxylate) (15 g, 0.066 mol), 5 wt % Ru/C catalyst (0.177 g, Aldrich Chemical Company) and methanol (100 g) into a 300 mL volume stainless steel Parr reactor, and seal the reactor. Purge the reactor 5 times with nitrogen gas (40 psig), then pressurize the reactor with H₂ gas to 650 psig. Raise temperature of contents in the reactor to 120° C. Adjust reactor pressure to 900 psig with additional H₂ gas. Maintain pressure at 890 psig-900 psig by addition of H₂ gas. After a total reaction time of 300 minutes, cool reactor contents and filter them to remove the catalyst. GC analysis and GC-MS analysis of the product reveals that dimethyl cyclohexane-2,5-diol-1,4-dicarboxylate (also referred to as dimethyl 2,5-dihydroxy-cyclohexane dicarboxylate is produced as four diastereomers and has less than 1 mol % of the bicyclic lactone by-product. The major diastereomer is a compound of formula (II-1) that has the structure (1) shown below as determined by X-ray crystallography:

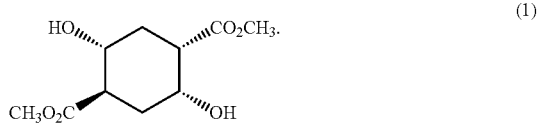

Figure 2:
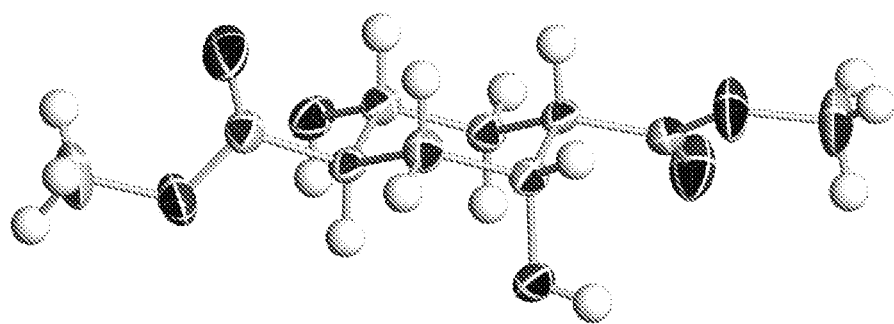
FIG. 2 shows an Oak Ridge Thermal Ellipsoid Plot (ORTEP) depiction of a single crystal structure derived by x-ray analysis of the major diastereomer (1) of Example 2, which major diastereomer (1) is chemoselectively produced with Ru/C as a dual-function supported metal catalyst and has a conformation that naturally inhibits bicyclic lactone by-product formation.

The ORTEP plot of the x-ray crystal structure of compound (1) is shown in FIG. 2.

Example 3

Condensed Process

Load dimethyl cyclohexane-2,5-dione-1,4-dicarboxylate (15.1 g, 0.066 mol), 5 wt % Ru/C catalyst (0.200 g, Aldrich Chemical) and methanol (90 g) into a 300 mL volume stainless steel Parr reactor. Purge the reactor 5 times with nitrogen gas (45 psig), then pressurize the reactor with H₂ gas to 700 psig. Heat contents of the reactor to 120° C. Adjust reactor pressure to 900 psig with additional H₂ gas. Maintain reactor pressure at 890 psig-900 psig by addition of H₂ gas. After a total reaction time of 180 minutes, cool reactor contents to ambient temperature and vent the reactor. (If desired, in a separate non-invention run, repeat the foregoing procedure and then heat reactor contents to 200° C. for 720 minutes without a dehydration catalyst (e.g., without sodium acetate) to show by GC analysis that there is no formation of dimethyl dihydrobenzene-1,4-dicarboxylate (i.e., dimethyl cyclohexa-1,4-diene dicarboxylate); dimethyl terephthalate; or by-product dimethyl cyclohexene-1,4-dicarboxylate). Add sodium acetate (0.98 g) to the reactor. Purge the reactor 5 times with nitrogen gas (45 psig), then heat contents to 200° C. After a 1200 minute run time, analyze an aliquot of the reactor contents by GC (area %) and find the contents to contain dimethyl dihydrobenzene-1,4-dicarboxylate (i.e., dimethyl cyclohexa-1,4-diene dicarboxylate diastereomer (A), (7.3%); and dimethyl cyclohexa-1,4-diene dicarboxylate diastereomer (B), (12.8%)); dimethyl terephthalate (29.9%); and by-product dimethyl cyclohexene-1,4-dicarboxylate (30.5%). Continue reaction for an additional 800 minutes at 200° C., and reanalyze an aliquot of the contents by GC (area %) and find the contents contain dimethyl dihydrobenzene-1,4-dicarboxylate (i.e., dimethyl cyclohexa-1,4-diene dicarboxylate diastereomer (A), (3.9%); and dimethyl cyclohexa-1,4-diene dicarboxylate diastereomer (B), (9.4%)); dimethyl terephthalate (34.2%); and by-product dimethyl cyclohexene-1,4-dicarboxylate (34.8%).

Example 4

Condensed Process

Load dimethyl cyclohexane-2,5-dione-1,4-dicarboxylate (14.98 g, 0.065 mol), Ni-3288 (1.09 g, Engelhard product code 0474128, containing about 50 wt % nickel on silica alumina) and methanol (85 g) into a 300 mL volume stainless steel Parr reactor. Purge the reactor 5 times with nitrogen gas (45 psig), then pressurize the reactor with H₂ gas to 700 psig. Heat contents of the sealed reactor to 120° C. Adjust reactor pressure to 900 psig with additional H₂ gas. Maintain pressure at 890 psig-900 psig by addition of H₂ gas. After a total reaction time (including heating up) of 600 minutes, cool reactor contents to ambient temperature and vent the reactor. Add 0.445 g of sodium acetate dissolved in 2.0 g of water and 3.0 g of methanol. Reseal the reactor and heat contents to 200°

C. for a 1200 minute run time (including heating up). Cool down, and then vent reactor and filter contents to remove catalyst, then strip off methanol using a rotary evaporator to give 11.8 g of an off-white solid containing by GC 14.3 area % dimethyl terephthalate.

Dissolve a portion (4.12 g) of the off-white solid in ethylene glycol dimethyl ether (97.1 g) solvent. Load the solution and 5% Pd/C (0.238 g, Johnson-Matthey A-11210-5) into a three necked round bottom flask. Heat contents of the flask at 160° C. for 7 hours, and cool. Add additional 5% Pd/C (0.30 g, Johnson-Matthey A-11210-5). Heat the contents for an additional 8 hours (heating time total of 15 hours), cool contents, and analyze by GC to show 63 area % dimethyl terephthalate (not counting solvent).

Examples 5 to 8

Repeat Examples 1 to 4, respectively, except substitute the TCI America-sourced dimethyl cyclohexane-2,5-dione-1,4-dicarboxylate with a dimethyl biocyclohexane-2,5-dione-1,4-dicarboxylate prepared from dimethyl biosuccinic acid (i.e., a dimethyl ester of biosuccinic acid prepared from biomass). The dimethyl biocyclohexane-2,5-dione-1,4-dicarboxylate and succeeding biomass-derived intermediate compounds and dimethyl terephthalate prepared therefrom will be tested according to ASTM D6866-10 and will exhibit a detectable amount of carbon-14 of up to about 1 part per trillion.

As shown by the Examples, the present invention provides the condensed and chemoselective processes and compositions of matter prepared thereby. The present invention has at least one of the aforementioned advantages.

What is claimed is:

1. A condensed process for preparing a dialkyl terephthalate, the condensed process comprising a one-pot portion comprising steps (a) to (c): (a) contacting a mixture comprising dialkyl cyclohexane-2,5-dione-1,4-dicarboxylate and an oxygen-containing solvent with hydrogen (H2) gas and a hydrogenating effective amount of a dual-function supported metal catalyst under hydrogenating effective conditions to give a dialkyl cyclohexane-2,5-diol-1,4-dicarboxylate, wherein the dual-function supported metal catalyst comprises a metal that can facilitate reduction and dehydrogenation and the metal is deposited on a solid support; (b) contacting the dialkyl cyclohexane-2,5-diol-1,4-dicarboxylate with a dehydrating effective amount of a dehydration catalyst under dehydrating effective conditions to give dialkyl dihydrobenzene-1,4-dicarboxylate; and (c) the dialkyl dihydrobenzene-1,4-dicarboxylate is dehydrogenated via the dual-function supported metal catalyst from step (a); wherein steps (a) to (c) are performed in a same reactor and the oxygen-containing solvent of step (a) is carried through and also employed in steps (b) and (c).

2. The condensed process as in claim 1, wherein the dialkyl cyclohexane-2,5-diol-1,4-dicarboxylate has less than 5 weight percent of a bicyclic lactone by-product.

3. The process as in claim 1, wherein the metal of the dual-function supported metal catalyst is Ir, Ni, Ru, Rh, Pd, Pt, or a combination thereof.

* * * * *